(12) United States Patent
Yamato et al.

(10) Patent No.: US 9,395,380 B2
(45) Date of Patent: Jul. 19, 2016

(54) SPECIMEN PROCESSING APPARATUS THAT DETERMINES WHETHER A MOVEABLE SECTION WAS MOVED WHEN A MOVING OPERATION HAD BEEN STOPPED

(75) Inventors: Takashi Yamato, Kakogawa (JP); Hiroshi Kurono, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 495 days.

(21) Appl. No.: 12/842,566

(22) Filed: Jul. 23, 2010

(65) Prior Publication Data

US 2011/0020948 A1    Jan. 27, 2011

(30) Foreign Application Priority Data

Jul. 24, 2009   (JP) .................................. 2009-172945

(51) Int. Cl.
| | |
|---|---|
| *G01N 35/02* | (2006.01) |
| *G01N 35/00* | (2006.01) |
| *G05D 3/12* | (2006.01) |
| *G01N 35/10* | (2006.01) |

(52) U.S. Cl.
CPC .......... *G01N 35/025* (2013.01); *G01N 35/0092* (2013.01); *G01N 35/1011* (2013.01); *G05D 3/12* (2013.01); *Y10T 436/25* (2015.01)

(58) Field of Classification Search
None
See application file for complete search history.

(56) References Cited

U.S. PATENT DOCUMENTS

| | | | |
|---|---|---|---|
| 2005/0281707 A1 | 12/2005 | Nakaya et al. | |
| 2007/0065945 A1* | 3/2007 | sIGRIST | G01N 35/1011 436/43 |
| 2008/0011106 A1 | 1/2008 | Kitagawa et al. | |
| 2008/0014118 A1 | 1/2008 | Kitagawa et al. | |

FOREIGN PATENT DOCUMENTS

| | | |
|---|---|---|
| CN | 101097223 A | 1/2008 |
| JP | 2001-327195 A | 11/2001 |
| JP | 2001327195 A | 11/2001 |
| JP | 3122073 U | 6/2006 |
| JP | 200889616 A | 4/2008 |
| JP | 2008-122417 A | 5/2008 |

* cited by examiner

*Primary Examiner* — Yelena G Gakh
*Assistant Examiner* — Michelle Adams
(74) *Attorney, Agent, or Firm* — Sughrue Mion, PLLC

(57) ABSTRACT

A specimen processing apparatus comprising: a specimen processing section which includes a movable section and processes a specimen by moving the movable section; and a controller for determining whether the movable section was moved while a specimen processing operation by the specimen processing section was stopped, and controlling the specimen processing section to perform a preparing operation for starting the specimen processing operation based on the determination result, is disclosed. A control method for a specimen processing apparatus is also disclosed.

22 Claims, 10 Drawing Sheets

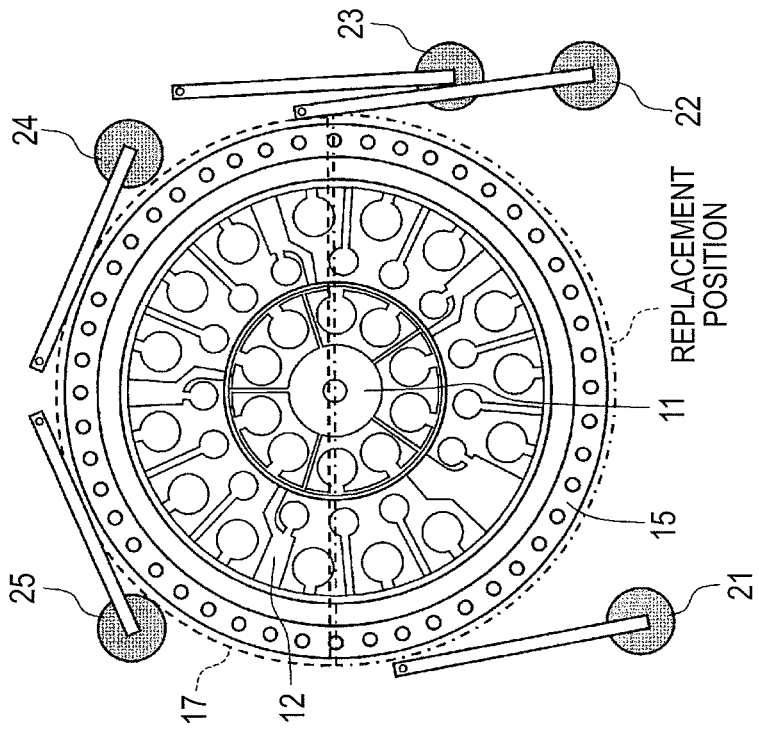
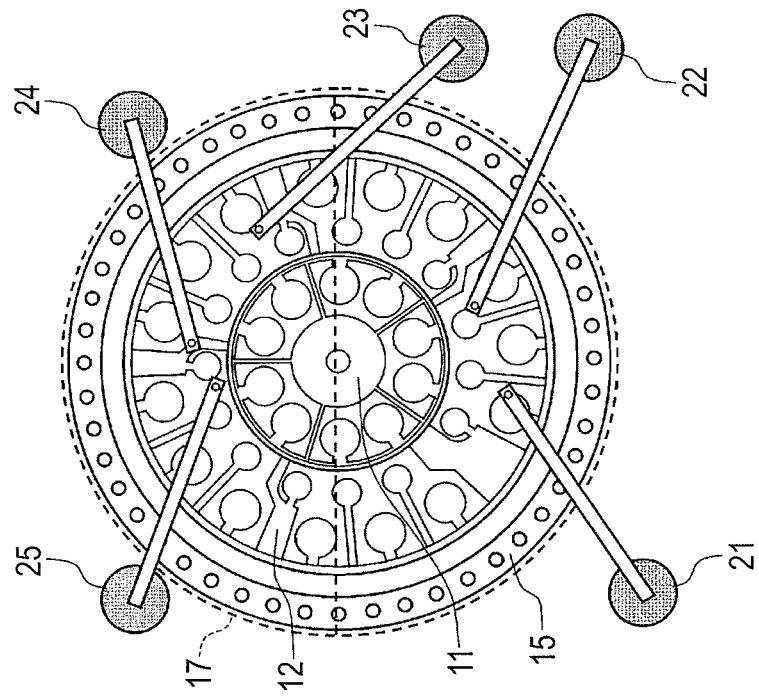

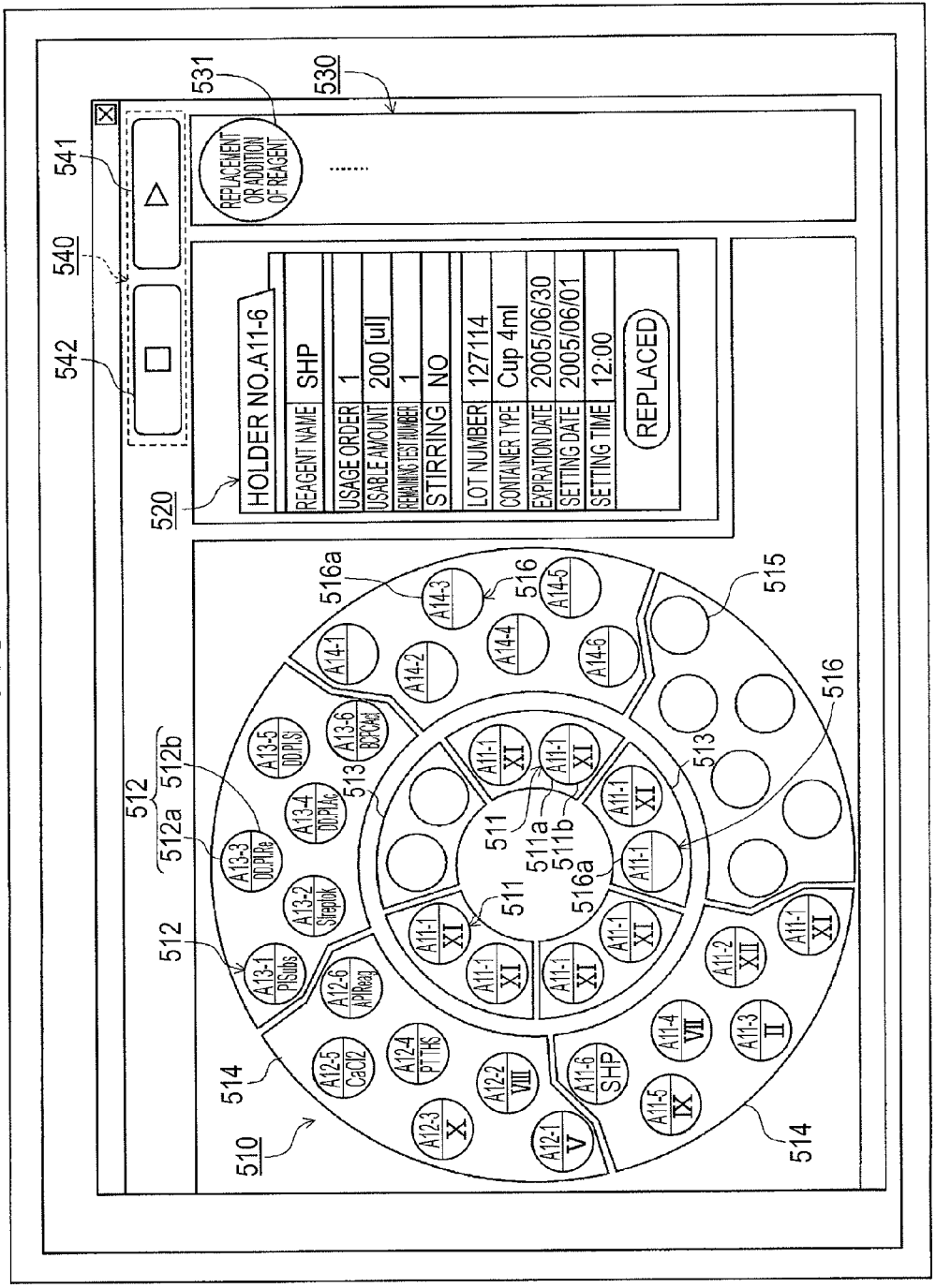

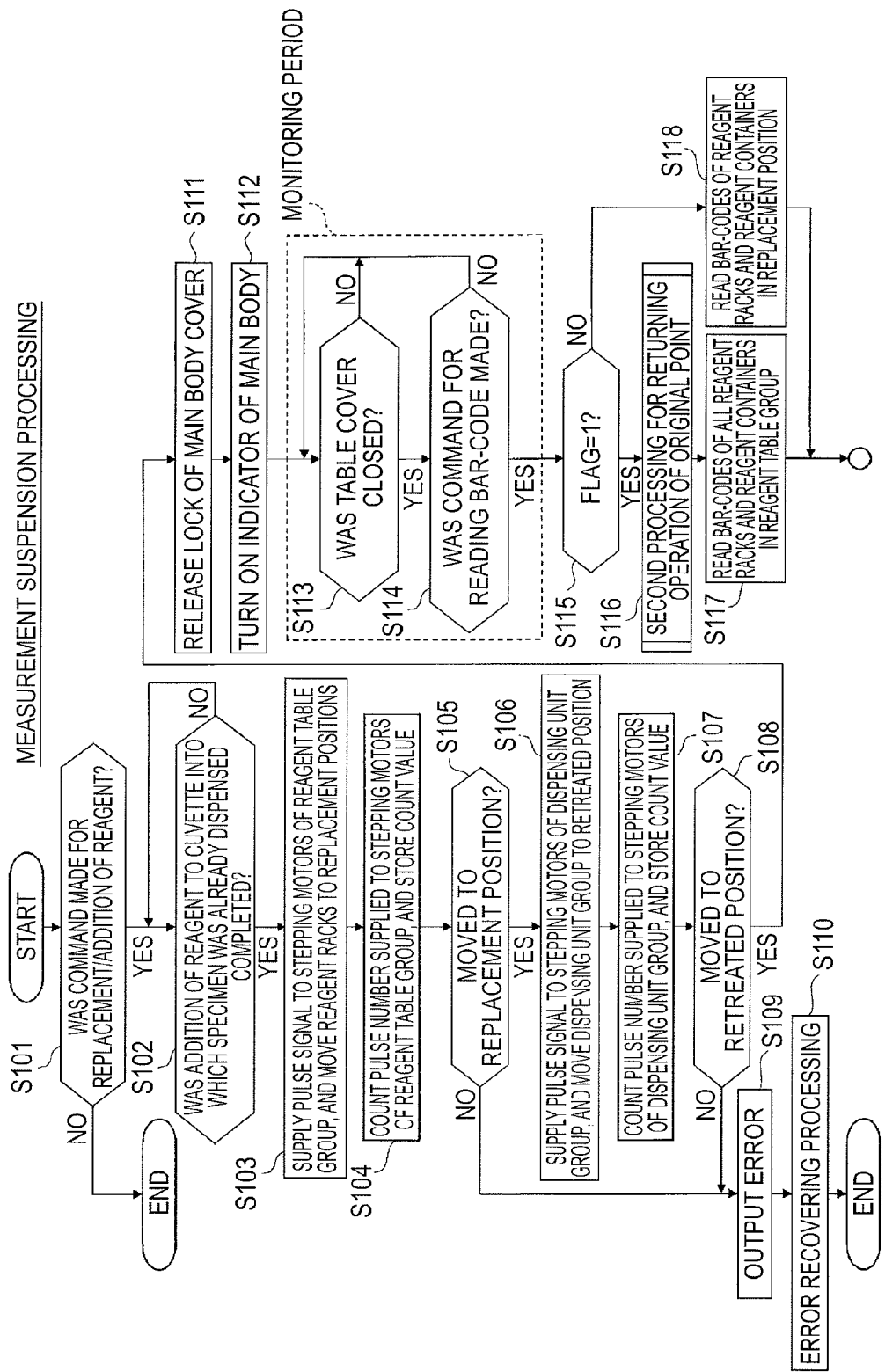

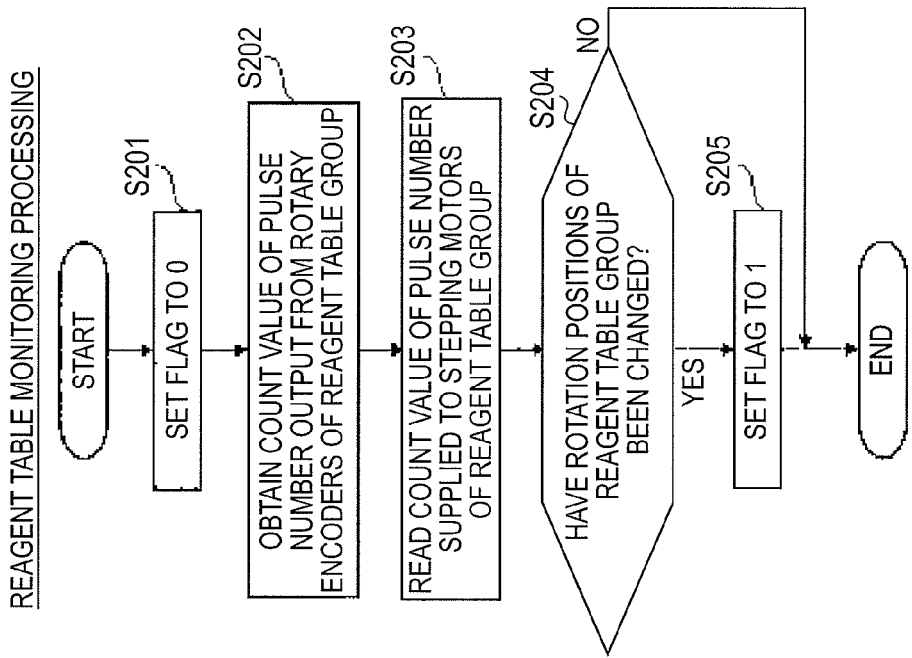
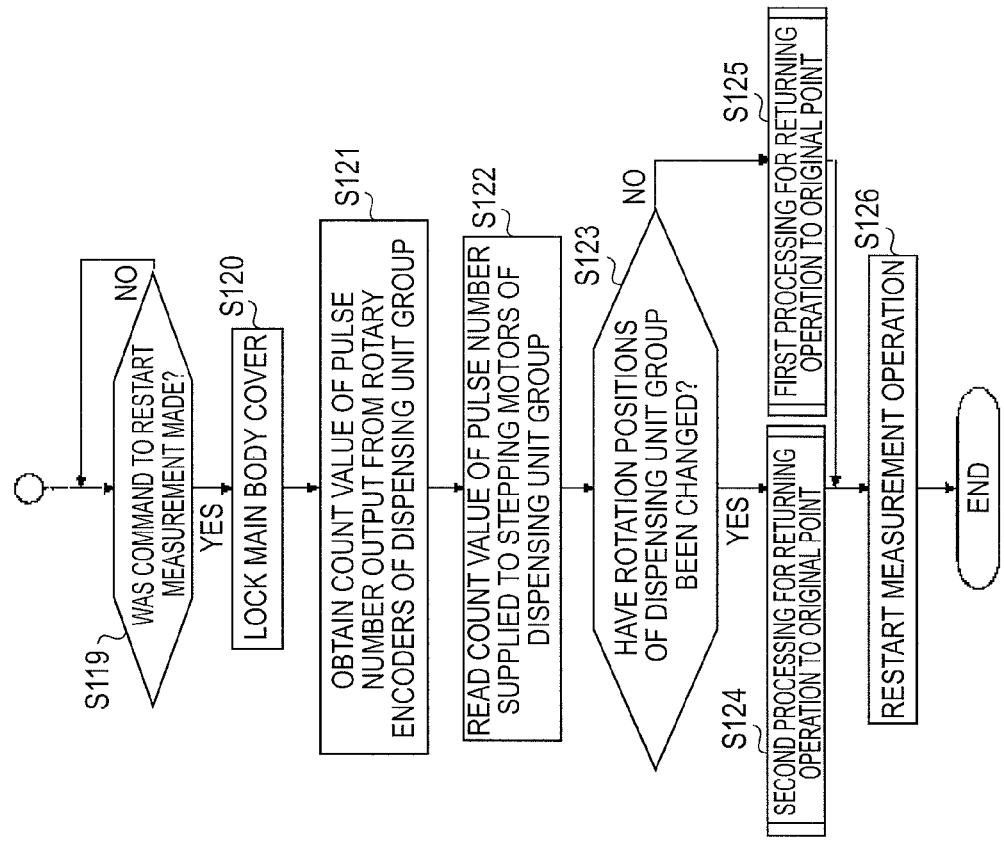

SPECIMEN PROCESSING APPARATUS THAT DETERMINES WHETHER A MOVEABLE SECTION WAS MOVED WHEN A MOVING OPERATION HAD BEEN STOPPED

FIELD OF THE INVENTION

The present invention relates to a specimen processing apparatus for processing a specimen such as blood, urine, or the like, and a control method for the same.

BACKGROUND

Conventionally, an automatic analyzing apparatus for analyzing a specimen such as blood, urine, or the like using a reagent has been known. According to such an automatic analyzing apparatus, a measurement sample prepared by mixing a specimen and a reagent is measured by a measurement section, and the component and the like of the specimen are analyzed based on the measurement result. The reagent is contained in a reagent container, and dispensed using a pipette or the like. When an amount of the reagent contained in the reagent container gets smaller, a user replaces the reagent container.

An automatic analyzing apparatus for replacing a reagent container easily has been disclosed in Japanese Laid-Open Patent Publication No. 2008-122417. This automatic analyzing apparatus is provided with a plurality of reagent discs on which reagent containers are placed, a reagent probe for suctioning a reagent from the reagent container placed on the respective reagent discs, and the like. When receiving a command for the replacement of the reagent during the execution of a measurement operation, this automatic analyzing apparatus stops the reagent disc for the reagent container to be replaced. Thereafter, when the replacement operation for the reagent container by a user is completed, the automatic analyzing apparatus restarts the reagent disc which has been stopped.

However, according to the automatic analyzing apparatus described in Japanese Laid-Open Patent Publication No. 2008-122417, there is a fear that a finger of the user or the like may get in contact with a movable section such as the reagent disc, the reagent probe or the like during the operation for the replacement of the reagent. If the reagent disc or the reagent probe or the like is moved by this contact, there is a fear that a malfunction may occur in the measurement operation after the release from this suspension.

SUMMARY OF THE INVENTION

The scope of the present invention is defined solely by the appended claims, and is not affected to any degree by the statements within this summary.

A first aspect of the present invention is a specimen processing apparatus comprising: a specimen processing section which includes a movable section and processes a specimen by moving the movable section; and a controller for determining whether the movable section was moved while a specimen processing operation by the specimen processing section was stopped, and controlling the specimen processing section to perform a preparing operation for starting the specimen processing operation based on the determination result.

A second aspect of the present invention is a specimen processing apparatus comprising: a specimen processing section which includes a movable section and processes a specimen by moving the movable section; and an information processing section for monitoring the movable section, wherein the information processing section determines whether the movable section was moved while the specimen processing operation by the specimen processing section was stopped, and the specimen processing section controls the specimen processing section to perform a preparing operation for starting a specimen processing operation based on the determination result by the information processing section.

A third aspect of the present invention is a control method for a specimen processing apparatus, comprising: stopping a movable section of a specimen processing section; determining whether the movable section was moved while a specimen processing operation by the specimen processing section was stopped; and executing a first preparing operation or a second preparing operation for starting the specimen processing operation based on the determination result.

BRIEF DESCRIPTION OF THE DRAWINGS

FIG. 4A is a diagram illustrating a procedure for a replacement or an addition of a reagent according to an embodiment.

FIG. 4B is a diagram illustrating a procedure for a replacement or an addition of a reagent according to an embodiment.

FIG. 7 is a diagram showing an example of a screen displayed on a display section of an information processing apparatus according to an embodiment.

FIG. 8 is a flow chart showing a measurement suspension processing according to an embodiment.

FIG. 9A is a flowchart showing a measurement suspension processing according to an embodiment.

FIG. 9B is a flowchart showing a measurement suspension processing according to an embodiment.

DETAILED DESCRIPTION OF THE PREFERRED EMBODIMENTS

In the present embodiment, the "stop" of the specimen processing operation is a concept including the "suspension" of the specimen processing operation. That is, the "stop" of the specimen processing operation widely includes a case in which the specimen processing operation by a specimen processing section is stopped such as a time period after the power activation and until the start of the specimen processing, a time period after the completion of the specimen processing operation and until the next start of the specimen processing operation, and the like, in addition to the case in which the specimen processing operation is forcibly "stopped" in the course of the specimen processing operation.

In the present embodiment, the present invention is applied to a specimen analyzing apparatus for optically measuring and analyzing a specimen (blood) by irradiating a light beam to the specimen to be measured which has been prepared by adding a reagent to blood, and using a coagulation method, a chromogenic substrate method, an immunoturbidimetric method, and a condensation method.

Hereinafter, a description will be made of the specimen analyzing apparatus according to the embodiment with reference to the drawings.

Figure 1:
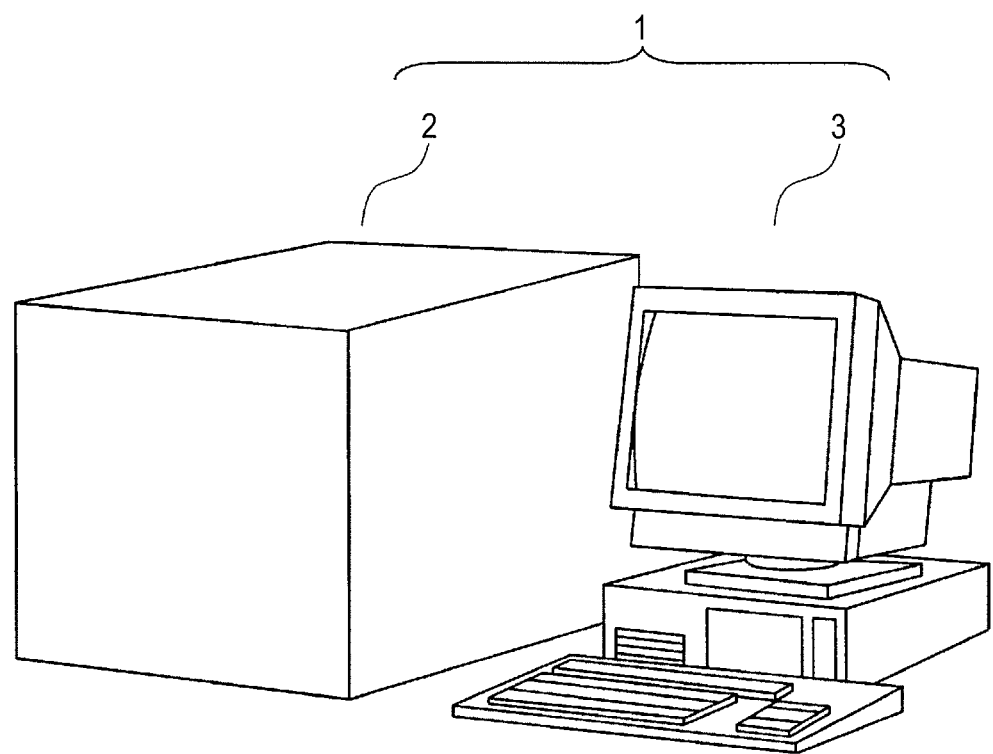
FIG. 1 is a diagram showing a configuration of a specimen analyzing apparatus according to an embodiment.

FIG. 1 is a diagram showing a configuration of a specimen analyzing apparatus 1 according to an embodiment of the present invention. The specimen analyzing apparatus 1 includes a measurement apparatus 2 for optically measuring components included in the specimen (blood), and an information processing apparatus 3 for analyzing measurement data of the measurement apparatus 2 and providing an operation command to the measurement apparatus 2.

Figure 2:
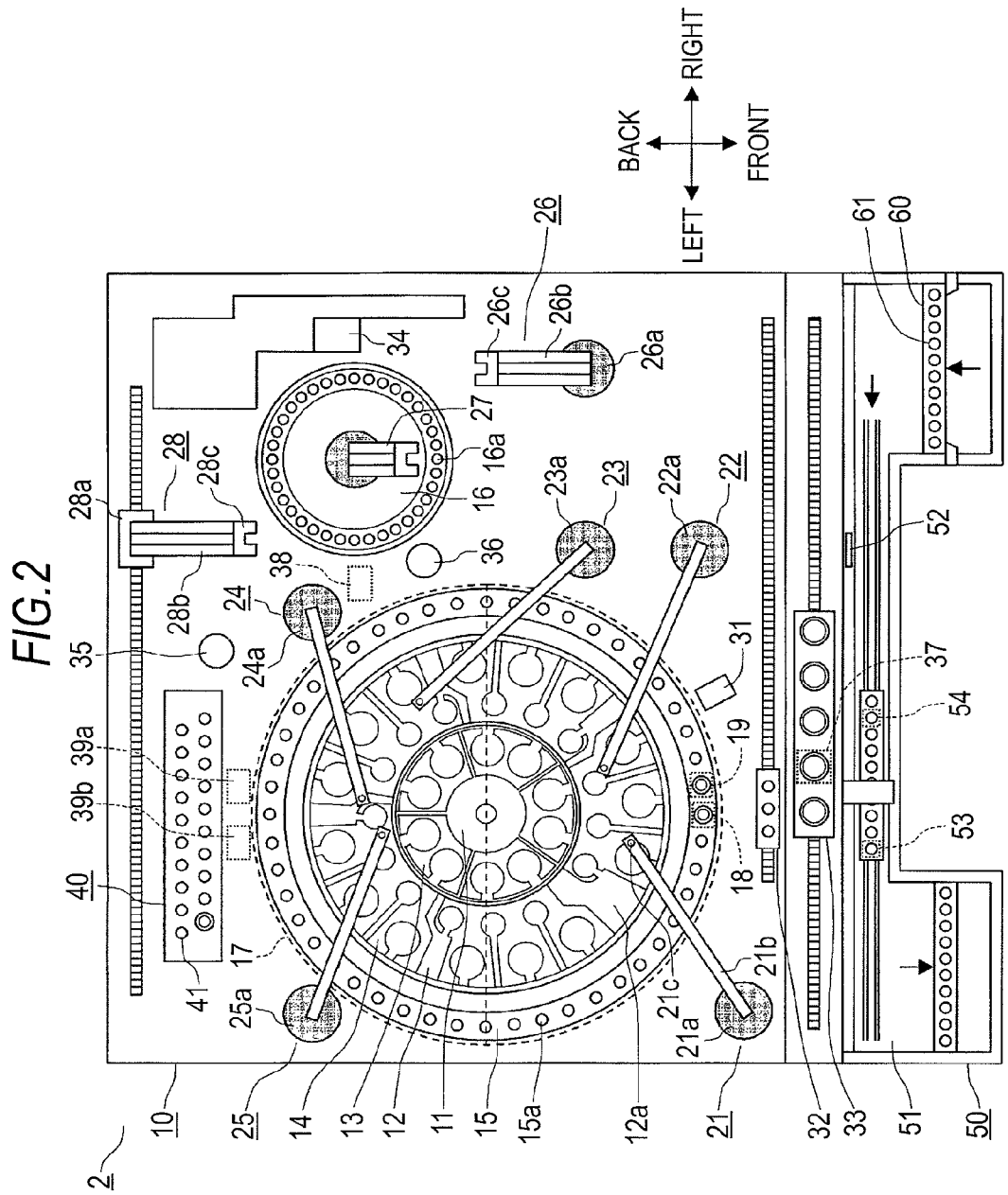
FIG. 2 is a plan view showing a schematic configuration of the inside of a measurement apparatus according to an embodiment.

FIG. 2 is a plan view showing a schematic configuration of the inside of the measurement apparatus 2 when seen from an upper direction. The measurement apparatus 2 includes a measurement unit 10, a detection unit 40, and a transport unit 50.

A measurement unit 10 includes a first reagent table 11, a second reagent table 12, a first container rack 13, a second container rack 14, a cuvette table 15, a warming table 16, a table cover 17, a first specimen dispensing unit 21, a second specimen dispensing unit 22, a first reagent dispensing unit 23, a second reagent dispensing unit 24, a third reagent dispensing unit 25, a first catcher unit 26, a second catcher unit 27, a third catcher unit 28, a reagent bar-code reader 31, a cuvette transporter 32, a diluent transporter 33, a cuvette port 34, a waste port 35, and a waste port 36.

The first reagent table 11, the second reagent table 12, the cuvette table 15, and the warming table 16 are circular tables, each of which is independently rotated and driven in both of the clockwise and counterclockwise directions. These tables are rotated and driven respectively by stepping motors 311a, 311b, 313, and 314 (see FIG. 5) arranged on the back sides of the lower surfaces.

As shown in FIG. 2, five first container racks 13 and five second container racks 14 are detachably arranged on the upper surfaces of the first reagent table 11 and the second reagent table 12, respectively. In the first container racks 13 and the second container racks 14, holding sections for holding reagent containers are formed. The reagent bar-code reader 31 is positioned outside the second reagent table, and the first reagent table 11 is positioned inside the second reagent table 12.

In addition, when the five second container racks 14 are arranged in the second reagent table 12, a gap 12a from among the gaps between adjacent second container racks 14 has larger clearance as compared with the other gaps as shown in FIG. 2. With this configuration, the reagent bar-code reader 31 can read bar-code information on the first container racks 13 arranged in the first reagent table 11 and on the reagent containers contained therein, via the gap 12a with a larger clearance compared with the other gaps.

Here, a description will be made of the configurations of the first container rack 13 and the second container rack 14 and the procedure in which the bar-code information attached to these container racks is obtained, with reference to the perspective views shown in FIGS. 3A and 3B.

Figure 3A:
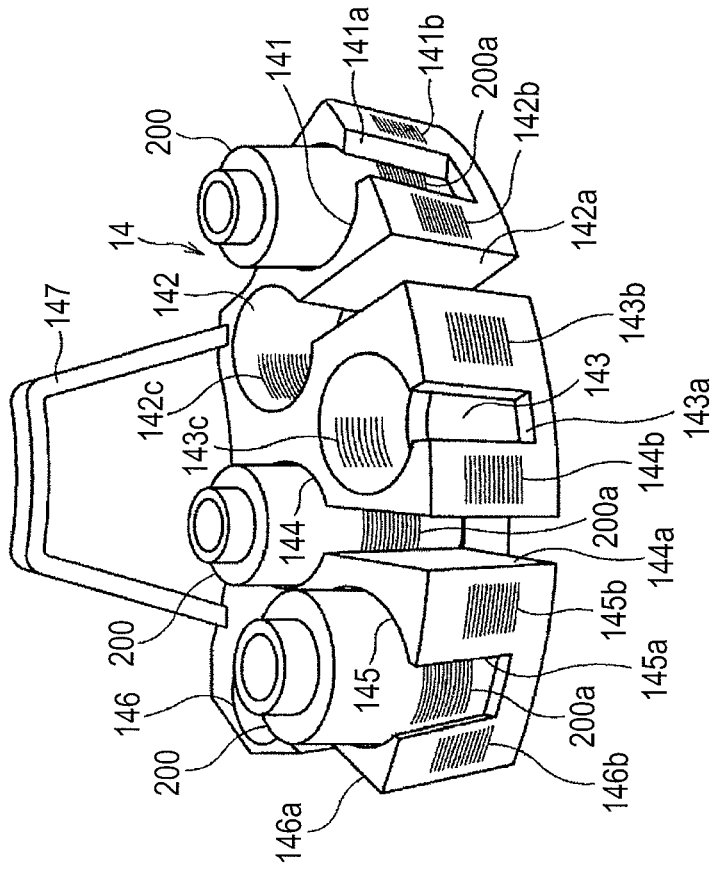
FIG. 3A is a diagram showing a configuration of a container rack according to an embodiment.

As shown in FIG. 3A, the first container rack 13 includes two holding sections 131 and 132 for holding cylindrical reagent containers 200, notch sections 131a and 132a which are respectively provided in the front surfaces of the holding sections 131 and 132, and a gripping section 133 which is provided so as to upwardly protrude. The holding sections 131 and 132 have containable parts with substantially circular shapes when seen from an upper direction so as to hold the reagent containers 200. In addition, when holding a container with a smaller outer shape as compared with the inner diameters of the holding sections 131 and 132, the first container rack 13 stably holds such a container using an additional adapter or the like.

Bar-code labels 131b and 132b are attached to the outer circumferential surfaces of the holding sections 131 and 132, respectively. In addition, bar-code labels are also attached to the inner circumferential surfaces of the holding sections 131 and 132, respectively. A bar-code label 200a is attached to the reagent container 200. FIG. 3A shows only a bar-code label 132c attached to the inner circumferential surface of the holding section 132 from among the bar-codes attached to the inner circumferential surfaces of the holding sections 131 and 132.

Figure 3B:
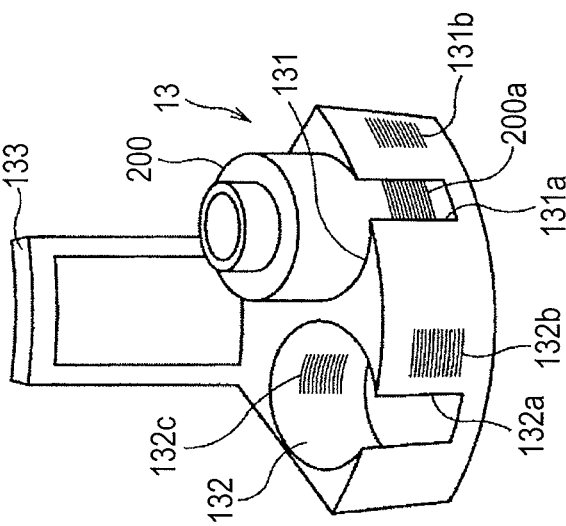
FIG. 3B is a diagram showing a configuration of a container rack according to an embodiment.

As shown in FIG. 3B, the second container rack 14 includes six holding sections 141 to 146 for holding cylindrical reagent containers 200, notch sections 141a to 146a which are respectively provided in the front surfaces of the holding sections 141 to 146, and a gripping section 147 which is provided so as to upwardly protrude. The holding sections 141 to 146 have containable parts with substantially circular shapes when seen from an upper direction so as to hold the reagent containers 200. In addition, when holding a container with a smaller outer shape as compared with the inner diameters of the holding sections 141 to 146, the second container rack 14 stably holds such a container using an additional adapter or the like.

Bar-code labels 141b to 146b are attached to the outer circumferential surfaces of the holding sections 141 to 146, respectively. In addition, bar-code labels are also attached to the inner circumferential surfaces of the holding sections 141 to 146, respectively. The bar-code label 200a is attached to the reagent container 200. FIG. 3B shows only bar-code labels 142c and 143c attached to the inner circumferential surface of the holding sections 142 and 143 from among the bar-code labels attached to the inner circumferential surfaces of the holding sections 141 to 146.

Next, a description will be made of the procedure in which the bar-code labels attached to the first container rack 13, the second container rack 14, and the reagent container 200 are read. In addition, the reagent bar-code reader 31 reads the bar-code labels from the front direction in FIGS. 3A and 3B.

First, the first reagent table and the second reagent table are rotated at a predetermined speed in a predetermined direction, and the bar-code labels attached to the outer circumferential surface of a predetermined holding section is read by the bar-code reader 31. With this operation, it is recognized that this holding section corresponds to which holding section in which container rack.

Subsequently, the bar-code positioned in the notch section of this holding section is read. At this time, the bar-code label attached to the reagent container 200 is read when the reagent container 200 is contained, and the bar-code label attached to the inner circumferential surface of the holding section is read when the reagent container 200 is not contained. In this manner, it is identified whether or not the reagent container 200 is contained in the holding section. Moreover, when the reagent container 200 is contained in the holding section, the type of the reagent contained in the reagent container 200 is identified based on the bar-code information read from the bar-code label 200a.

As shown in FIG. 2, a plurality of cuvette holding holes 15a and 16a are formed respectively in the cuvette table 15 and the warming table 16 along their circumference. When the cuvettes are set in the cuvette holding holes 15a and 16a, these cuvettes are moved in the circumferential positions along with the rotations of the cuvette table 15 and the warming table 16. In addition, the warming table 16 warms the cuvettes set in the holding holes 16a at a predetermined temperature.

The table cover 17 is provided so as to cover the upper surfaces of the first reagent table 11, the second reagent table 12, and the cuvette table 15. The table cover 17 has a folding mechanism in its center portion such that only the front half thereof can be opened. In addition, the table cover 17 is provided with a plurality of holes. Dispensing by the first specimen dispensing unit 21, the second specimen dispensing unit 22, the first reagent dispensing unit 23, the second reagent dispensing unit 24, and the third reagent dispensing unit 25 are performed through this plurality of holes.

The first specimen dispensing unit 21 includes a supporting section 21a, an arm 21b, and a dispensing section 21c as shown in FIG. 2. The supporting section 21a is rotated and driven by a stepping motor 312a (see FIG. 5) arranged on the back side of the lower surface. The supporting section 21a supports the arm 21b, and the arm 21b is driven in the vertical direction by the stepping motor 312a. The dispensing section 21c is attached to a leading end of the arm 21b, and has a pipette. This pipette is used to suction and discharge the specimen.

When the supporting section 21a is rotated and driven, the dispensing section 21c is moved on a circumference around the supporting section 21a. The dispensing section 21c suctions the specimen, which exists directly below the dispensing section 21c, in the specimen suctioning position, and discharges the specimen into the cuvette, which exists directly below the dispensing section 21c, in the specimen discharging position. In addition, the second specimen dispensing unit 22, the first reagent dispensing unit 23, the second reagent dispensing unit 24, and the third reagent dispensing unit 25 have the same configuration as that of the first specimen dispensing unit 21. That is, the second specimen dispensing unit 22 is provided with a supporting section 22a, and the supporting section 22a is rotated and driven by a stepping motor 312b (see FIG. 5) arranged on the back side of the lower surface. In addition, the first reagent dispensing unit 23, the second reagent dispensing unit 24, and the third reagent dispensing unit 25 are provided with a supporting section 23a, a supporting section 24a, and a supporting section 25a, respectively. Moreover, the supporting section 23a, the supporting section 24a, and the supporting section 25a are rotated and driven by a stepping motor 312c, a stepping motor 312d, and a stepping motor 312e (see FIG. 5) arranged on the back sides of the lower surfaces, respectively.

The first catcher unit 26 includes a supporting section 26a for supporting an arm 26b, the arm 26b which can be extended and contracted, and a gripping section 26c as shown in FIG. 2. The supporting section 26a is rotated and driven by a stepping motor 315a (see FIG. 5) arranged on the backside of the lower surface. The gripping section 26c is attached to the leading end of the arm 26b, and can grip the cuvette. In addition, the second catcher unit 27 has the same configuration as that of the first catcher unit 26, and is rotated by a stepping motor 315b (see FIG. 5).

The third catcher unit 28 includes a supporting section 28a for supporting an arm 28b, the arm 28b which can be extended and contracted, and a gripping section 28c which is attached to the leading end of the arm 28b as shown in FIG. 2. The supporting section 28a is driven along a rail arranged in a horizontal direction. The gripping section 28c can grip the cuvette.

The reagent bar-code reader 31 reads a bar-code label attached to the first container rack 13 and the second container rack 14, and the bar-code labels 200a attached to the reagent containers 200 contained in these racks. In addition, the first reagent table 11 and the second reagent table 12 can be independently rotated. The bar-code label attached to the first container rack 13 and the bar-code labels 200a attached to the reagent containers 200 contained in the first container rack 13 are read via the gap 12a when the gap 12a of the second reagent table 12 reaches the position in front of the reagent bar-code reader 31.

The cuvette transporter 32 and the diluent transporter 33 are driven on the rails in the horizontal direction. In addition, holes for holding the cuvettes and the diluent containers are provided in the cuvette transporter 32 and the diluent transporter 33, respectively.

The cuvette port 34 is always supplied with new cuvettes. The new cuvettes are set in the holes of the cuvette transporter 32 for holding the cuvettes and in the cuvette holding hole 15a of the cuvette table 15 by the first catcher unit 26 and the second catcher unit 27. The waste ports 35 and 36 are the holes for disposing of the unnecessary cuvettes after the completion of the analysis.

The detection unit 40 is provided with ten holding holes 41 for containing cuvettes on the upper surface, and a detection section on the backside of the lower surface. When the cuvettes are set in the holding holes 41, optical information is detected from the reagent for the measurement inside the cuvettes, using the detection section.

The transport unit 50 is provided with a transport passage 51 and a specimen bar-code reader 52. The bottom surface of the transport passage 51 includes a right tank area on its right side, a connecting area in its center, and a left tank area on its left side, and is formed in a U-shape. The specimen bar-code reader 52 reads bar-code labels attached to a specimen containers 61 contained in a specimen rack 60 which is transported through the connecting area.

Next, a description will be made of a series of operations for analyzing the specimen.

The specimen rack 60 containing a plurality of specimen containers 61 is set in the right tank area of the transport passage 51. The specimen rack 60 is moved backward in the right tank area, and then moved in the left direction through the connecting area. At this time, the bar-code labels attached to the specimen containers 61 are read by the specimen bar-code reader 52. Subsequently, the specimen rack 60 is positioned in a predetermined position in the connecting area. When the suctioning of the specimen is completed in the connecting area, the specimen rack 60 is moved in the left direction through the connecting area, and then moved forward in the left tank area.

The first specimen dispensing unit 21 suctions the specimen in the specimen container 61 which is positioned at a predetermined specimen suctioning position 53 in the connecting area of the transport passage 51. The specimen suctioned by the first specimen dispensing unit 21 is discharged into the cuvette set in the cuvette holding hole 15a positioned in a specimen discharging position 18 in a position in front of the cuvette table 15.

The second specimen dispensing unit 22 suctions the specimen contained in the cuvette in a specimen suctioning position 19, or the specimen in the specimen container 61 positioned at a predetermined specimen suctioning position 54 in the connecting area of the transport passage 51. The specimen suctioned by the second specimen dispensing unit 22 is discharged into the cuvette set in the cuvette transporter 32. In addition, the second specimen dispensing unit 22 can suction the diluent set in the diluent transporter 33. In this case, the specimen dispensing unit 22 suctions the diluent at a diluent suctioning position 37 before the suctioning of the specimen, and then suctions the specimen at the specimen suctioning position 19 or 54.

The cuvette transporter 32 is driven on the rail in the right direction at a predetermined timing, when the specimen is discharged into the cuvette contained therein. Subsequently, the cuvette, which contains the specimen, set in the cuvette transporter 32 is gripped by the first catcher unit 26, and set in the cuvette holding hole 16a of the warming table 16.

Subsequently, the second catcher unit 27 grips the cuvette, which contains the specimen, set in the holding hole 16a, and moves it to a reagent discharging position 38. Here, the first reagent dispensing unit 23 suctions a reagent (a first reagent) within the predetermined reagent container 200 positioned in the first reagent table 11 or in the second reagent table 12, and discharges the reagent at the reagent discharging position 38. When the reagent is discharged in this manner, the second catcher unit 27 stirs this cuvette, and sets it in the cuvette holding hole 16a of the warming table again.

The cuvette held by the cuvette holding hole 16a of the warming table 16 is then gripped by the third catcher unit 28, and positioned at a reagent discharging position 39a or 39b. Here, the second reagent dispensing unit 24 and the third reagent dispensing unit 25 suction a reagent (a second reagent) in the predetermined reagent container 200 positioned in the first reagent table 11 or in the second reagent table 12, and discharge it at the reagent discharging positions 39a and 39b, respectively. When the reagent is discharged in this manner, the third catcher unit 28 sets the cuvette, into which the reagent is discharged, in the holding hole 41 of the detection unit 40. Thereafter, optical information is detected from the reagent for the measurement, which is contained in the cuvette, in the detection unit 40.

Although both of the mixing of the reagent (first reagent) by the first reagent dispensing unit 23 and the mixing of the reagent (second reagent) by the second reagent dispensing unit 24 and the third reagent dispensing unit 25 are performed here, mixing of the first reagent may not be performed in some cases depending upon the contents of the analysis. In such a case, the mixing step of the first reagent is skipped, and the optical information is detected after only the mixing of the second reagent is performed.

The unnecessary cuvette after the completion of the detection by the detection unit 40 is moved up to the position directly over the waste port 35 while being gripped by the third catcher unit 28, and disposed of in the waste port 35. In addition, the cuvette held in the cuvette holding hole 15a of the cuvette table 15 is also positioned at a place close to the second catcher unit 27 by rotating the cuvette table 15, when it becomes unnecessary after the completion of the analysis. The second catcher unit 27 grips the unnecessary cuvette held in the cuvette holding hole 15a, and disposes of it in the waste port 36.

FIGS. 4A and 4B are diagrams illustrating procedures in the case of performing the replacement or the addition of the reagent. FIG. 4A is a diagram showing an ordinary usage state, and FIG. 4B is a diagram showing the state in which the replacement or the addition of the reagent is performed.

As shown in FIG. 4A, the table cover 17 covers the upper surfaces of the first reagent table 11, the second reagent table 12 (hereinafter, referred to as a "reagent table group"), and the cuvette table 15 in the ordinary usage state. At this time, the first specimen dispensing unit 21, the second specimen dispensing unit 22, the first reagent dispensing unit 23, the second reagent dispensing unit 24, and the third reagent dispensing unit 25 (hereinafter, referred to as a "dispensing unit group") perform the dispensing through a plurality of holes provided in the table cover 17.

As shown in FIG. 4B, when the replacement or the addition of the reagent is performed, the dispensing unit group is retreated up to a position outside an area which is covered by the table cover 17 (hereinafter, referred to as a "retreated position") as shown in FIG. 4A. Thereafter, the table cover 17 is folded at its center portion. With this operation, the state turns into the one in which only the upper half area of the reagent table group and the cuvette table 15 is covered with the table cover 17 as shown in FIG. 4B (the part surrounded by a dotted line represents the area which is covered with the table cover 17, and the part surrounded by a dashed line represents the area which is not covered with the table cover 17). At this time, since there occurs an area which is not covered with the table cover 17 (hereinafter, referred to as a "replacement position"), a user can replace or add the reagent through such a replacement position. That is, the user takes out the first reagent rack 13 and the second reagent rack 14 through the replacement position, replaces or adds the reagent, and then sets the reagent racks to the reagent tables again. Alternatively, the user directly replaces or adds the reagent with respect to the reagent containers 200 arranged in the reagent racks.

Figure 5:
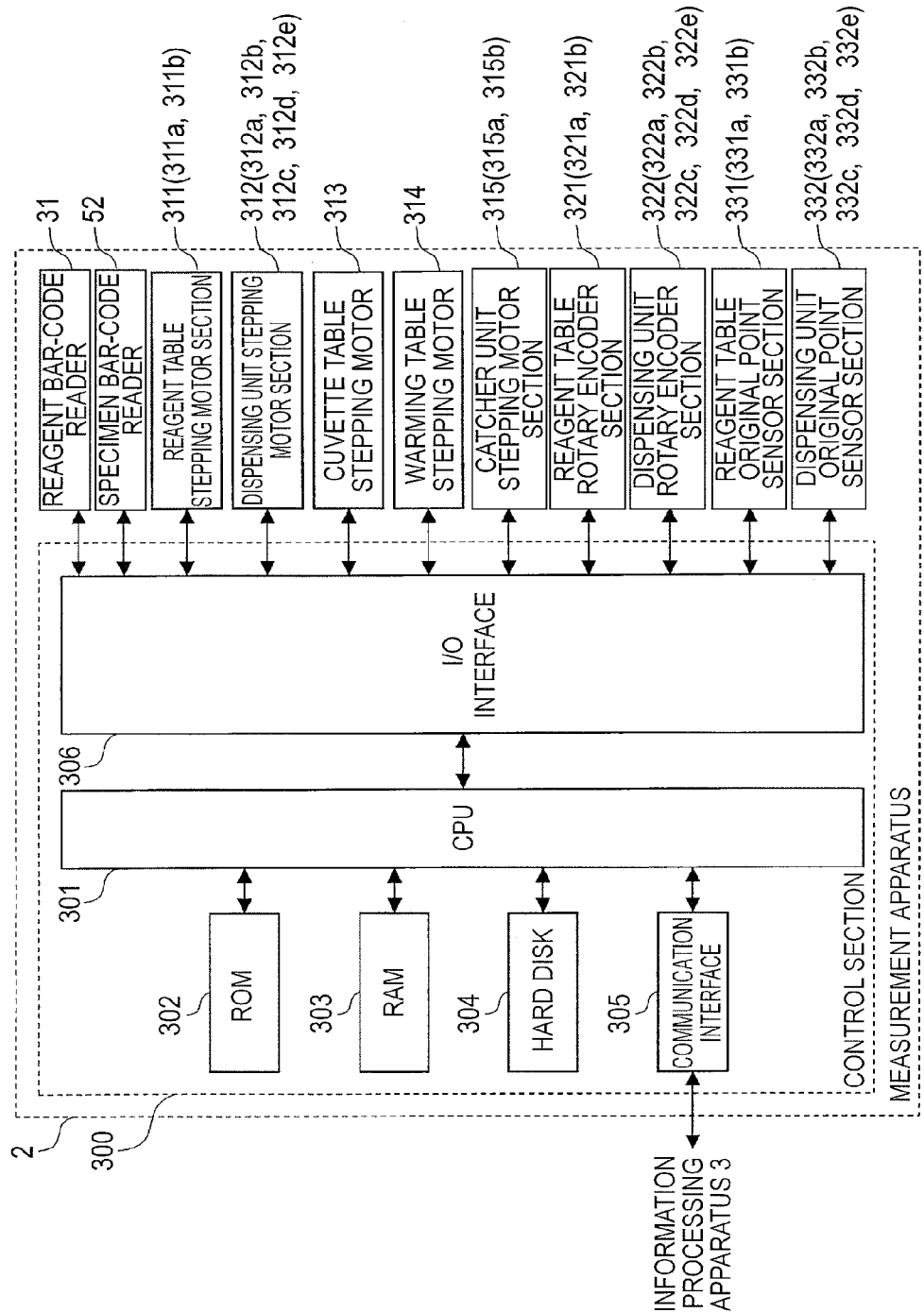
FIG. 5 is a diagram showing a circuit configuration of a measurement apparatus according to an embodiment.

FIG. 5 is a diagram showing a circuit configuration of a measurement apparatus 2.

The measurement apparatus 2 includes a control section 300, the reagent bar-code reader 31, the specimen bar-code reader 52, a reagent table stepping motor section 311, a dispensing unit stepping motor section 312, the cuvette table stepping motor 313, the warming table stepping motor 314, a catcher unit stepping motor section 315, a reagent table rotary encoder section 321, a dispensing unit rotary encoder section 322, a reagent table original point sensor section 331, and a dispensing unit original point sensor section 332. The control section 300 includes a CPU 301, a ROM 302, a RAM 303, a hard disk 304, a communication interface 305, and an I/O interface 306.

The CPU 301 executes a computer program stored in the ROM 302 and a computer program loaded in the RAM 303. The RAM 303 is used to read the computer programs stored in the ROM 302 and the hard disk 304. In addition, when these computer programs are executed, the RAM 303 is used as a work area of the CPU 301. Various computer programs to be executed by the CPU 301 such as an operating system, an application program, and the like, and data used for executing the computer programs are installed on the hard disk 304. In addition, it is possible to exchange the data with the information processing apparatus 3 by the communication interface 305.

The CPU 301 controls the reagent bar-code reader 31, the specimen bar-code reader 52, the reagent table stepping motor section 311, the dispensing unit stepping motor section 312, the cuvette table stepping motor 313, the warming table stepping motor 314, the catcher unit stepping motor section 315, the reagent table rotary encoder section 321, the dispensing unit rotary encoder section 322, the reagent table original point sensor section 331, and the dispensing unit original point sensor section 332 through the I/O interface 306.

The reagent table stepping motor section 311 includes the stepping motor 311a for rotating and driving the first reagent table 11, and the stepping motor 311b for rotating and driving the second reagent table 12 independently from the first reagent table 11. The dispensing unit stepping motor section 312 includes stepping motors 312a, 312b, 312c, 312d, and 312e for independently rotating and driving the supporting section 21a of the first specimen dispensing unit 21, a supporting section 22a of the second specimen dispensing unit 22, the supporting section 23a of the first reagent dispensing unit 23, the supporting section 24a of the second reagent dispensing unit 24, and the supporting section 25a of the third reagent dispensing unit 25, respectively. The catcher unit stepping motor section 315 includes the stepping motor 315a for rotating and driving the supporting section 26a of the first catcher unit 26, and the stepping motor 315b for rotating the second catcher unit 27.

The reagent table rotary encoder section 321 includes a rotary encoder 321a arranged in the stepping motor 311a of the first reagent table 11, and a rotary encoder 321b arranged in the stepping motor 311b of the second reagent table 12. The dispensing unit rotary encoder section 322 includes rotary encoders 322a, 322b, 322c, 322d, and 322e arranged in the respective stepping motors 312a, 312b, 312c, 312d, and 312e of the first specimen dispensing unit 21, the second specimen dispensing unit 22, the first reagent dispensing unit 23, the second reagent dispensing unit 24, and the third reagent dispensing unit 25. In addition, an incremental rotary encoder is used here. This rotary encoder is configured to output a pulse signal in accordance with a rotation displacement amount of the stepping motors, and can detect the rotation amount of the stepping motors by counting the pulse number output from the rotary encoder.

The reagent table original point sensor section 331 includes original point sensors 331a and 331b for detecting that the respective rotation positions of the stepping motor 311a of the first reagent table 11 and the stepping motor 311b of the second reagent table 12 are in the original point position. The dispensing unit original point sensor section 332 includes original point sensors 332a, 332b, 332c, 332d, and 332e for detecting that the respective rotation positions of the stepping motors 312a, 312b, 312c, 312d, and 312e of the first specimen dispensing unit 21, the second specimen dispensing unit 22, the first reagent dispensing unit 23, the second reagent dispensing unit 24, and the third reagent dispensing unit 25 are in the original point position.

Figure 6:
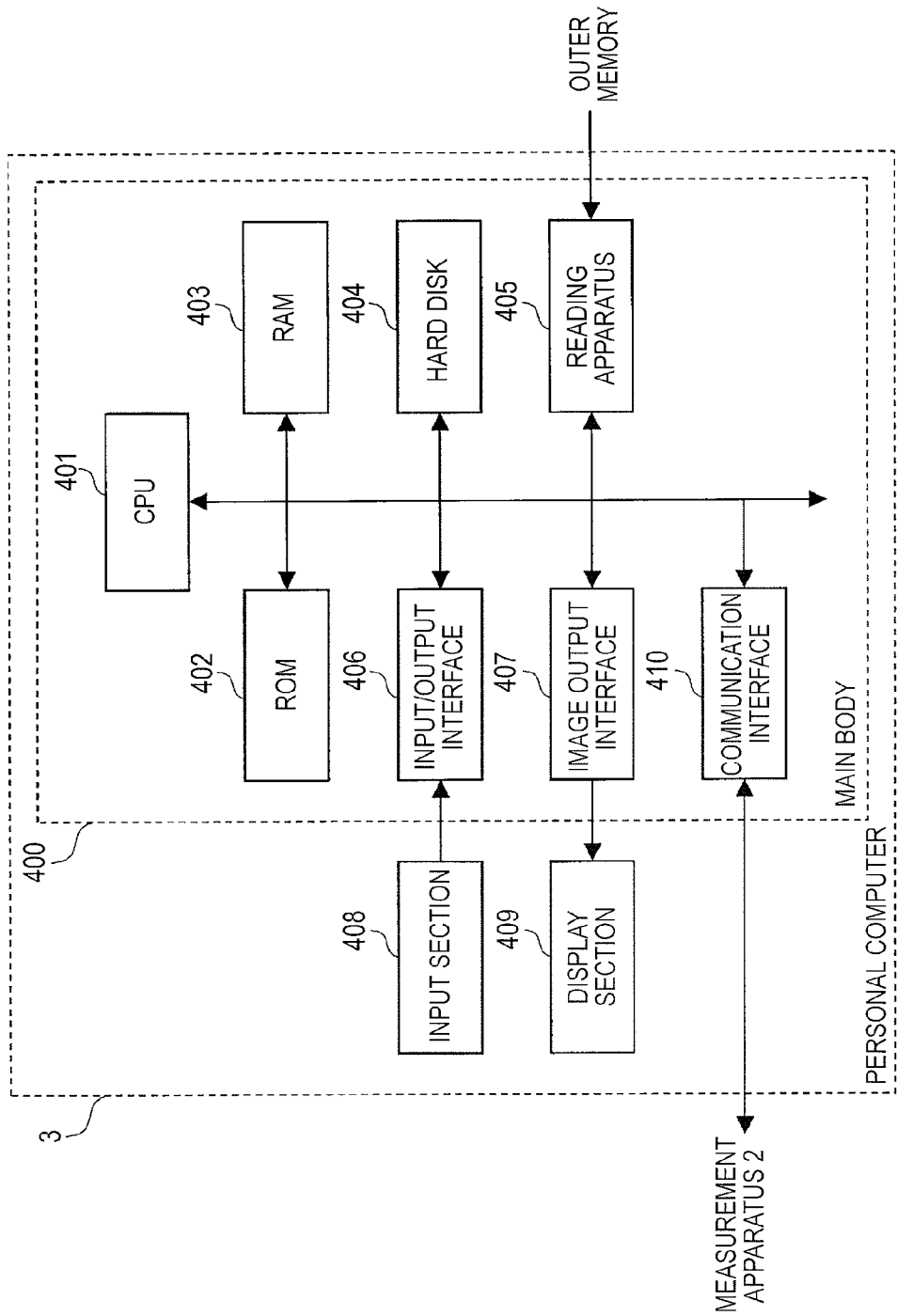
FIG. 6 is a diagram showing a circuit configuration of an information processing apparatus according to an embodiment.

FIG. 6 is a diagram showing a circuit configuration of the information processing apparatus 3.

The information processing apparatus 3 is constituted by a personal computer, and includes a main body 400, an input section 408, and a display section 409. The main body 400 includes a CPU 401, a ROM 402, a RAM 403, a hard disk 404, a reading apparatus 405, an input/output interface 406, an image output interface 407, and a communication interface 410.

The CPU 401 executes a computer program stored in the ROM 402, and a computer program loaded in the RAM 403. The RAM 403 is used to read the computer programs stored in the ROM 402 and the hard disk 404. In addition, the RAM 403 is also used as a work area of the CPU 401 when these computer programs are executed.

Various computer programs to be executed by the CPU 401 such as an operating system, an application program, and the like, and data used for executing the computer programs are installed on the hard disk 404. That is, a display program for receiving a reagent state from the measurement apparatus 2 and displaying a remaining amount of the reagent or the like on the display section 409 as a message or the like, and an operating program for operating the measurement apparatus 2 while following the operation command for the replacement or the addition of the reagent are installed in the hard disk 404.

The reading apparatus 405 includes a CD drive, a DVD drive, or the like, and can read the computer programs and data recorded in a recording medium. The input section 408, which is constituted by a mouse and a keyboard, is connected to the input/output interface 406, and data is input to the information processing apparatus 3 when the user uses the input section 408. The image output interface 407 is connected to the display section 409, which is constituted by a display, and the like, and outputs a video signal in accordance with the image data to the display section 409. The display section 409 displays an image based on the input video signal. In addition, it is possible to exchange data with the measurement apparatus 2 by the communication interface 410.

FIG. 7 is a diagram showing an example of a screen displayed on the display section 409 of the information processing apparatus 3. The screen displayed on the display section 409 of the information processing apparatus 3 includes an arrangement display area 510, a detailed information display area 520, an operation command display area 530, and an operation determination display area 540.

The arrangement display area 510 is for displaying the positions of the first container racks 13 and the second container racks 14 arranged in the first reagent table 11 and the second reagent table 12, and the arrangement state of the reagent containers 200.

A maximum of 10 first reagent marks 511, which are displayed correspondingly to the arrangement state of the reagents with respect to the first reagent table 11, and a maximum of 30 second reagent marks 512, which are displayed correspondingly to the arrangement state of the reagents with respect to the second reagent table 12, are displayed in the arrangement display area 510. The first reagent marks 511 include a position display section 511a for displaying a position, and a name displaying section 511b for displaying the name of the reagent. In the same manner, the second reagent marks 512 include a position display section 512a for displaying a position, and a name displaying section 512b for displaying the name of the reagent.

The position information of the reagent, which is displayed on the position display section 511a of the first reagent mark 511 and the position display section 512a of the second reagent mark 512, is displayed by reading the bar-code labels attached to the first container rack 13 and the second container rack 14 using the reagent bar-code reader 31. The name of the reagent, which is displayed on the name display sections 511b and 512b, is displayed by reading the bar-code label 200a attached to the reagent container 200 containing the reagent, using the reagent bar-code reader 31. That is, the name of the reagent is displayed on the name display sections 511b and 512b by referring to a reagent master or the like stored in the hard disk 404 based on the bar-code information included in the bar-code label 200a.

The first reagent mark 511 is split and displayed by first rack marks 513 corresponding to the five first container racks 13 arranged in the first reagent table 11. The second reagent mark 512 is split and displayed by second rack marks 514 corresponding to the five second container racks 14 arranged in the second reagent table 12. With this configuration, it is possible to visually confirm in which reagent table a predetermined reagent is arranged, in which container rack the predetermined reagent is arranged, and in which position the predetermined reagent is arranged.

When a container rack is not arranged in the first reagent table 11 and the second reagent table 12, a circular rack non-arrangement mark 515, inside which nothing is displayed, is displayed. Moreover, when container racks are arranged in the first reagent table 11 and the second reagent table 12, a reagent non-arrangement mark 516 is displayed for an area corresponding to a position where reagent container 200 containing the reagent is not arranged. The reagent non-arrangement mark 516 includes a position display section 516*a* displaying position information.

When the first reagent mark 511 or the second reagent mark 512 is selected, the detailed information display area 520 displays the detailed information regarding the content of the reagent container 200 held at the selected selection mark position.

The operation command display area 530 includes a plurality of command types 531. The operation determination display area 540 includes an operation start button 541 and an operation stop button 542. When a user selects one of the command types 531 and then presses the operation start button 541, the operation selected by the command type 531 is executed. In addition, when the user presses the operation stop button 542, the operation being executed is stopped. The operation start button 541 is effectively displayed when the operation is executable, and a message is displayed on the screen so as to inform the user that the operation is non-executable when the operation start button 541 is pressed in the case when the operation is non-executable.

FIGS. 8, 9A, and 9B are diagrams showing the processing flows for the measurement suspension processing according to the present embodiment. The measurement suspension processing is executed when a user commands the replacement or the addition of the reagent through the information processing apparatus 3, when the operation stop button 542 is pressed during the measurement operation, or when the measurement apparatus 2 recognizes that the reagent runs out. That is, although the suspension of the measurement operation is determined depending on whether or not the user inputs the command for the replacement or the addition of the reagent in S101 of FIG. 8, the measurement suspension processing after S102 is also executed when the operation stop button 542 is pressed, or when the measurement apparatus 2 recognizes that the reagent runs out in addition to the illustrated example. Such a measurement suspension processing is performed under the control of the control section 300.

During measurement operations, when the replacement or the addition of the reagent is commanded by selecting the command type 531 of "the replacement/addition of the reagent" in the operation command display area 530 shown in FIG. 7 and pressing the operation start button 541 (S101: YES), the processing proceeds to S102. When such a command is not made (S101: NO), the processing flow ends. When such a command is made, a suctioning for new specimens performed by the specimen dispensing unit 21 and the specimen dispensing unit 22 is suspended.

If the reagent addition to the cuvette, to which the specimen was already dispensed, is completed after the suspension of the suctioning of the new specimens performed by the specimen dispensing unit 21 and the specimen dispensing unit 22 (S102: YES), the processing proceeds to S103. If the reagent addition to the cuvette, to which the specimen was already dispensed is not completed (S102: NO), the processing flow is put on standby until such a reagent addition is completed. When the reagent addition to the cuvette, to which the specimen was already dispensed, is completed, it is not necessary to drive the reagent table group and the dispensing unit group.

In S103, the stepping motors 311*a* and 311*b* (see FIG. 5) of the reagent table group are supplied with pulse signals, respectively, and the reagent table group is rotated and driven such that the reagent container for which the replacement or the addition of the reagent is commanded is positioned within the replacement position shown in FIG. 4B. When the replacement or the addition of the reagent is commanded without the designation of the reagent container to be replaced or added, the pulse signal is not supplied to the stepping motor of the reagent table group. When the measurement apparatus 2 recognizes that the reagent in the reagent container is running out, the reagent table group is rotated and driven such that such a reagent container is positioned within the replacement position.

In S104, the pulse is supplied to the stepping motors 311*a* and 311*b* of the reagent table group by the time that the reagent table group is rotated and driven so as to be positioned in the replacement position in S103. The count value of the pulse number corresponding to the rotation position from the original point position is updated based on the pulse number supplied at this time. Such a count value is updated and stored in the RAM 303 of the measurement apparatus 2 as needed. With such a configuration, it is possible to identify the rotation positions of the reagent table group after they are moved to the replacement positions, based on the count value stored in the RAM 303.

When the reagent table group is rotated and driven, and the reagent container, which is designated for the replacement or the addition of the reagent, is moved to the replacement position (S105: YES), the processing proceeds to S106. When such a reagent container is not moved to the replacement position (S105: NO), the processing proceeds to S109. In addition, whether the reagent container has been moved to the replacement position is determined depending, for example, on whether the count value of the pulse number from the above-mentioned original position has become the value corresponding to the replacement position.

In S106, the dispensing unit group is respectively supplied with the pulse signals, and is moved to the retreated position shown in FIG. 4B.

In S107, the number of the pulses, which was supplied to the stepping motors 312*a* to 312*e* (see FIG. 5) of the dispensing unit group when the dispensing unit group was moved to the retreated position in S106, is counted, and the count value of the pulse number corresponding to the rotation position from the original point position is updated based on the counted number of the pulses. This count value is updated and stored in the RAM 303 of the measurement apparatus 2 as needed. With this configuration, it is possible to identify the rotation positions of the dispensing unit group after they are moved to the retreated positions based on the count value stored in the RAM 303.

If the dispensing unit group has been moved to the retreated position (S108: YES), the processing proceeds to S111. When the dispensing unit group has not been moved to the retreated position (S108: NO), the processing proceeds to S109. Here, whether the dispensing unit group has been moved to the retreated position is determined depending, for example, on whether the count value of the pulse number from the above-mentioned original point position has become the value corresponding to the replacement position.

In S109, an error message is output to the display section 409 of the information processing apparatus 3 so as to inform that the movement of the reagent table group to the replacement position or the movement of the dispensing unit group to the retreated position is in a error state. In S110, an error recovering processing is executed so as to be able to start the restarting of the processing flow of the measurement suspension processing, and the processing flow is terminated.

If the reagent table group has been moved to the replacement position, and the dispensing unit group has been moved to the retreated position in this manner, the lock of the main body cover is released in S111, and the indicator of the main body is turned on in S112. With such a configuration, a user can know that replacement or the addition of the reagent can be performed by opening the main body cover of the measurement apparatus 2. Thereafter, the user opens the main body cover of the measurement apparatus 2, opens the table cover 17, and performs the replacement or the addition of the reagent.

If the replacement or the addition of the reagent by the user has been completed, and the table cover 17 has been closed (S113: YES), the processing proceeds to S114. If the table cover 17 has not been closed (S113: NO), the processing flow is put on standby until the table cover 17 is closed.

Thereafter, if the table cover 17 is closed (S113: YES), it is determined that the user has input the command for reading the bar-code label through the information processing apparatus 3 (S114). If the command for reading the bar-code label has been input (S114: YES), the processing proceeds to S115, and if the command for reading the bar-code label has not been input (S114: NO), the processing flow is put on standby until the command for reading the bar-code label is input.

Here, the following processing is performed in a parallel manner during the period from when the indicator of the main body is turned on (S112) to S115 (hereinafter, referred to as a "monitoring period"). This processing is repeatedly performed at an interval of once every 100 ms.

FIG. 9B is a diagram showing a processing flow of a processing performed during the monitoring period.

In S201, a flag value stored in the RAM 303 of the measurement apparatus 2 is set to 0. In S202, the count value of the pulse number output from the rotary encoder section 321 of the reagent table group is obtained. In S203, the count value stored in S104, that is, the count value of the pulse number supplied to the stepping motors 311a and 311b of the reagent table group is read.

The rotation position on the basis of the count value of the pulse number output from the rotary encoder section 321 of the reagent table group, which was obtained in S202, and the rotation position on the basis of the count value of the pulse number supplied to the stepping motors 311a and 311b of the reagent table group, which was stored in S104, are compared, and it is determined whether the rotation positions of the reagent table group have been changed from the replacement positions (S204). Here, if the rotation position of at least one reagent table has been changed from the replacement position (S204: YES), the processing proceeds to S205. That is, when it is determined that the reagent table group has been moved from the time point when it became possible to perform the replacement or the addition of the reagent, the processing proceeds to S205. In S205, the flag is set to 1, and the processing flow is terminated. In addition, when any of the rotation positions of the reagent tables have not been changed from the replacement position (S204: NO), the processing flow is terminated without changing the flag to 1.

Such a processing is repeatedly performed at short intervals of once every 100 ms during the monitoring period. If the position of the reagent table group is moved by the contact of the user's finger or the like at each period of performing processing, the flag value is set to 1 for the processing in the corresponding time. If the position of the reagent table group is not moved at all during the monitoring period, the flag value is still 0.

Referring again to FIG. 8, if the determination has been made to be YES in S114, then it is determined whether the flag value is 1 in S115. If the flag value is 1 (S115: YES), the processing proceeds to S116, and if the flag value is not 1 (S115: NO), the processing proceeds to S118.

In S116, a second processing for a returning operation to an original point is performed to match the original point positions of the reagent table group. With this processing, the rotation positions of the reagent table group are appropriately adjusted. The description will be made later regarding the second processing for the returning operation to the original point, with reference to FIGS. 10C and 10D. Such a returning operation to the original point may be performed only for the reagent table whose rotation position has been changed from the replacement position, or may be uniformly performed for all the reagent tables.

In S117, all the bar-code labels of all the reagent containers 200 and the reagent racks arranged in the reagent table group are read. In S118, the bar-code labels of all the reagent containers 200 and the reagent racks in the replacement position are read.

FIG. 9A is a diagram showing the processing flow following S117 and S118 shown in FIG. 8.

If the user inputs the command to restart the measurement through information processing apparatus 3 (S119: YES), the processing proceeds to S120. If the command to restart the measurement is not made (S119: NO), the processing flow is put on standby until the command is made.

In S120, the main body cover is locked. In S121, the count value of the pulse number output from the rotary encoder section 322 of the dispensing unit group is obtained. In S122, the count value stored in S107, that is, the count value of the pulse number supplied to the stepping motors 312a to 312e of the dispensing unit group is read.

The rotation position on the basis of the count value of the pulse number output from the rotary encoder section 322 of the dispensing unit group, which was obtained in S121, and the rotation position on the basis of the count value of the pulse number supplied to the stepping motors 312a to 312e of the dispensing unit group, which was stored in S107, are compared to determine whether the rotation positions of the dispensing unit group have been changed from the retreated position (S123). Here, if the rotation position of at least one dispensing unit has been changed from the retreated position (S123: YES), the processing proceeds to S124. That is, when it is determined that the dispensing unit group was moved since when it became possible to perform the replacement or the addition of the reagent, the processing proceeds to S124. When any rotation positions of the dispensing units have not been moved from the retreated position (S123: NO), the processing proceeds to S125.

In S124, the second processing for the returning operation to the original point is performed to match the original point positions of the dispensing unit group. With this operation, the rotation positions of the dispensing unit group are appropriately adjusted. In S125, the first processing for the returning operation to the original point is performed to match the original point positions of the dispensing unit group. With this operation, the rotation positions of the dispensing unit group are appropriately adjusted. In the first processing for the returning operation to the original point, the matching of the original point positions is simply performed as compared with the second processing for the returning operation to the original point.

That is, in the case in which a user touched the dispensing unit group, and the rotation positions of the dispensing unit group have been changed during the replacement or the addition of the reagent, the second processing for the returning operation to the original point with higher precision is performed. On the other hand, when the rotation positions of the dispensing unit group have not been changed, the rotation positions of the dispensing unit group are in the same state as that when they were appropriately recognized, and therefore, the first processing for the returning operation to the original point, by which it is possible to match the original point positions in a short time, is performed. The first processing for the returning operation to the original point will be described later with reference to FIG. 10.

In S126, the measurement operation is restarted, and the processing flow is terminated.

Figure 10C:
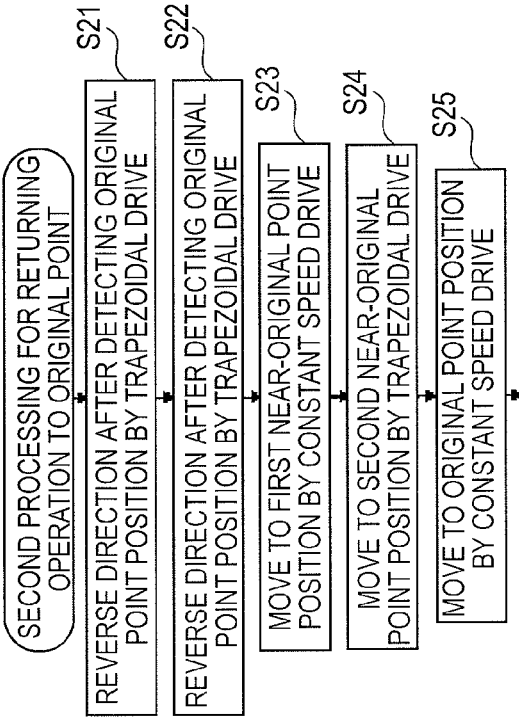
FIG. 10C is a diagram illustrating a processing content of a processing for a returning operation to an original point according to an embodiment.
Figure 10D:
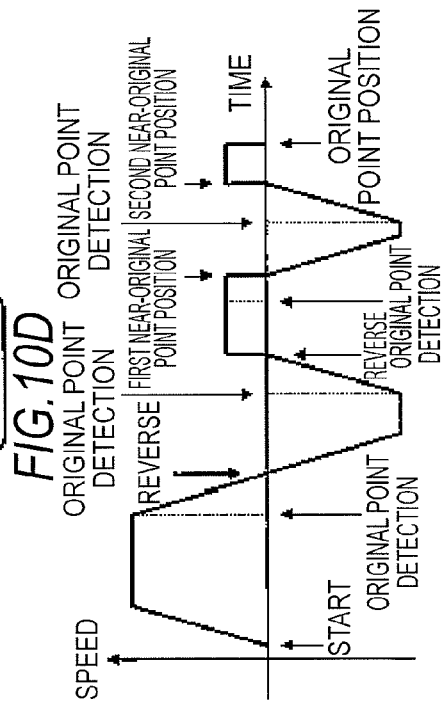
FIG. 10D is a diagram illustrating a processing content of a processing for a returning operation to an original point according to an embodiment.
Figure 10A:
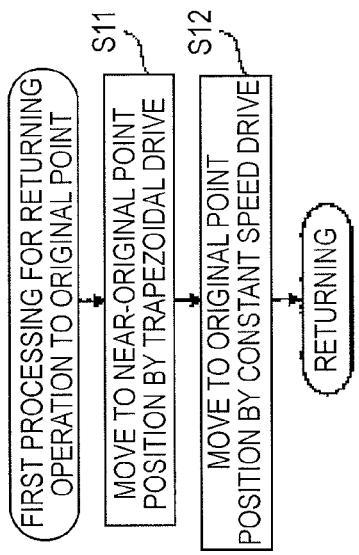
FIG. 10A is a diagram illustrating a processing content of a processing for a returning operation to an original point according to an embodiment.
Figure 10B:
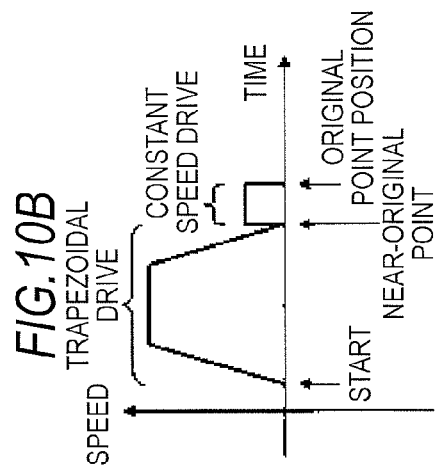
FIG. 10B is a diagram illustrating a processing content of a processing for a returning operation to an original point according to an embodiment.

FIGS. 10A to 10D are diagrams showing the processing contents of the first processing for the returning operation to the original point and the second processing for the returning operation to the original point. FIGS. 10A and 10B are diagrams showing the processing flow of the first processing for the returning operation to the original point and specific processing contents, respectively. FIGS. 10C and 10D are diagrams showing the processing flow of the second processing for the returning operation to the original point and specific processing contents, respectively. In FIGS. 10B and 10D, the horizontal axis represents the time, and the vertical axis represents the speed.

First, a trapezoidal drive and a constant speed drive will be described with reference to FIG. 10B.

The trapezoidal drive is a drive procedure in which the rotation speed of the stepping motor is increased with the passage of time, and becomes constant when it reaches a predetermined speed, and is decreased with the passage of time when it meets a predetermined condition, as shown in FIGS. 10B and 10D. In addition, the constant speed drive is a drive procedure in which the stepping motor is driven at a predetermined speed, and stopped when the speed meets a predetermined condition, as shown in FIGS. 10B and 10D.

As shown in FIG. 10A, in the first processing for the returning operation to the original point, the stepping motor is subjected to the trapezoidal drive, and the rotation position of the stepping motor is moved to a near-original point position in S11. Here, the near-original point position is a position from which the rotation position of the stepping motor can be appropriately adjusted to the original point position when the stepping motor is subjected to the constant speed drive from the near-original point position next time. The speed of the stepping motor is decreased at a predetermined rotation position before the near-original point position. In this manner, the rotation position of the stepping motor is positioned at the near-original point position when the trapezoidal drive is completed.

If the rotation position of the stepping motor has been matched to the near original point position, the stepping motor is then subjected to the constant speed drive in S12, and the rotation position of the stepping motor is eventually matched to the original point position. The first processing for the returning operation to the original point is performed in the case in which the rotation positions of the dispensing unit group have not been changed, as shown in S125 of FIG. 9A. That is, since the position information of the stepping motor is in the same state as that when it is appropriately recognized in the case in which the rotation positions of the dispensing unit group have not been changed, the first processing for the returning operation to the original point, which can perform the original point position matching in a shorter time, is employed.

As shown in FIGS. 10C and 10D, in the second processing for the returning operation to the original point, the stepping motor is subjected to the trapezoidal drive in S21, the speed of the stepping motor is decreased when it is detected that the rotation position of the stepping motor has passed the original point position (original point detection), and the rotation direction of the stepping motor is then reversed.

In S22, the stepping motor is subjected to the trapezoidal drive in the reverse direction with respect to the rotation direction in S21, the speed of the stepping motor is decreased if the original point has been detected again, and the rotation direction of the stepping motor is then reversed to shift to the constant drive.

In S23, the stepping motor is subjected to the constant speed drive in the reverse direction with respect to the rotation direction in S22, and the rotation direction of the stepping motor is reversed when the original point is detected again. At this time, the position at which the speed of the stepping motor becomes 0 becomes a first near-original point position. Here, the first near-original point position is a position from which the rotation position of the stepping motor can be matched to a second near-original point position, which is substantially the same position as the near-original point position shown in FIG. 10B, if the stepping motor is subjected to the trapezoidal drive from the first near-original point position next time.

In S24, the stepping motor is subjected to the trapezoidal drive, and the rotation direction of the stepping motor is reversed when the original point is detected. At this time, the position at which the speed of the stepping motor becomes 0 becomes the second near-original point position. In S25, the stepping motor is subjected to the constant speed drive, and the rotation position of the stepping motor is eventually matched to the original point position.

As described above, in the second processing for the returning operation to the original point, it is possible to more precisely match the rotation position to the original point position by performing more steps than that in the first processing for the returning operation to the original point. Accordingly, this is performed in the case in which the encoder values of the reagent table group and the dispensing unit group have been changed, as shown in S116 of FIG. 8 and S124 of FIG. 9A.

As described above, according to the present embodiment, the bar-code labels of all the reagent containers 200 and the reagent racks arranged in the reagent table group are read in the case in which the user touched the reagent table group when performing the replacement or the adding operation of the reagent, and the rotation positions of the reagent table group have been changed. With this configuration, it is possible to appropriately obtain the states of all the reagent racks and the reagent containers. On the other hand, the bar-code labels of all the reagent containers 200 and the reagent racks in the replacement position are read in the case in which the rotation positions of the reagent table group have not been changed. With this configuration, it is possible to obtain the states of the reagent racks and the reagent containers with a higher speed.

According to the present embodiment, the matching of the original point positions for the reagent table group is performed in the case in which the user touched the reagent table group when performing the replacement or the adding operation of the reagent, and the rotation positions of the reagent table group have been changed. With this configuration, it is possible to appropriately obtain the rotation positions of the reagent table group. On the other hand, the matching of the original point positions for the reagent table group is not performed in the case in which the rotation positions of the reagent table group have not been changed. With this configuration, it is possible to more rapidly restart the measurement operation.

According to the present embodiment, the second processing for the returning operation to the original point is performed in the case in which the user touched the dispensing unit group when performing the replacement or the adding operation of the reagent, and the rotation positions of the dispensing unit group have been changed. With this configuration, it is possible to appropriately adjust the rotation positions of the dispensing unit group. On the other hand, the first processing for returning operation to the original point is performed in the case in which the rotation positions of the dispensing unit group have not been changed. With this configuration, it is possible to perform the returning operation to the original point in a short time, and more rapidly restart the measurement operation.

Although the embodiment of the present invention was described above, the present invention is not limited thereto. In addition, the embodiment of the present invention can be modified in various manners in addition to the above configuration.

For example, although it was determined whether the rotation positions of the reagent table group and the dispensing unit group have been changed during the measurement suspension processing in the above embodiment, it is also applicable that the determination is made regarding the changes in the rotation positions of the cuvette table 15, the warming table 16, the first catcher unit 26, and the second catcher unit 27 (hereinafter, referred to as a "circumferential unit group") in addition to the rotation positions of the reagent table group and the dispensing unit group, and that a preparing operation for such a circumferential unit group is performed. In this case, a rotary encoder, which detects the rotation position of the stepping motor for rotating and driving the circumferential unit group, and an original point sensor, which detects that the rotation position of the stepping motor for rotating and driving the circumferential unit group is in the original point position, are arranged. With this configuration, it is possible to correct the rotation positions of the circumferential unit group even if the circumferential unit group is moved while the replacement or the adding operation of the reagent is being performed, and it is possible to smoothly restart the measurement operation.

In the above embodiment, it is determined whether or not a positional deviation occurred in the reagent dispensing unit and the like during the suspension of the measurement operation and in the reagent dispensing unit and the like at the time when the measurement operation was restarted, by counting the pulse number supplied to the stepping motor, storing the count value in memory, and determining whether or not the count value during the suspension of the measurement operation is different from the count value of the pulse number output from the rotary encoder until the measurement operation was restarted. However, the present invention is not limited thereto, and it is also applicable that the positional deviation of the reagent dispensing unit or the like is determined by obtaining the count value of the pulse number output from the rotary encoder until the measurement operation was suspended and the count value of the pulse number output from the rotary encoder until the measurement operation was restarted, respectively, and determining whether or not both values are different from each other.

In the above embodiment, the pulse number supplied to the stepping motors of the reagent table group and the dispensing unit group are counted every time that the measurement suspension processing is performed to obtain the count values corresponding to the replacement positions of the reagent table group and to the retreated positions of the dispensing unit group (S104 and S107 in FIG. 8). However, it is also applicable that the count values corresponding to these are stored in advance as default values in the hard disk 304 or the like when the replacement positions and the retreated positions are fixed to predetermined positions, and that these count values are compared with a count value of the pulse number output from the rotary encoder until now to determine the movement of the reagent table group and the dispensing unit group with respect to the replacement position and the retreated position. In this case, the information stored as the default values is not limited to the count values, and may be different position information representing the replacement position and the retreated position.

In the above embodiment, although the pulse number supplied to the stepping motors of the reagent table group and the dispensing unit group and the pulse number output from the rotary encoder are counted, and both count values are compared to determine the movement of the reagent table group and the dispensing unit group, it is also applicable that the movement of the reagent table group and the dispensing unit group is determined by another method. For example, the rotary encoder arranged in the respective stepping motors is replaced with an absolute type rotary encoder which outputs the rotation angle of the stepping motor as an absolute value. In this case, the rotation angle value output from the corresponding rotary encoder is changed if the reagent table group and the dispensing unit group are respectively moved from the replacement position and the retreated position, and the rotation angle value output from the rotary encoder is not changed if they are not moved. Accordingly, it is possible to be determined whether or not the reagent table group and the dispensing unit group have been respectively moved from the replacement position and the retreated position depending on whether or not the rotation angle value output from the rotary encoder has been changed.

It is also applicable that another processing is performed along with the above measurement suspension processing. For example, when the rotation positions of the dispensing unit group have been changed, there is a possibility that dust or the like has been adhered to the respective dispensing sections by a user's contact to the dispensing unit group. Accordingly, when it is determined that the rotation positions of the dispensing unit group was changed, a cleaning step for cleaning respective dispensing sections may be added before restarting the measurement operation.

In the above embodiment, the processing flow of the above measurement suspension processing was performed when the command for the replacement or the addition of the reagent was made by the user or when the measurement apparatus 2 recognized that the reagent was running out. However, the present invention is not limited thereto, and for example, it is also applicable to determine whether the rotation positions of the reagent table group and the dispensing unit group have been changed during the period between the time point at which an error was detected and the time point at which the measurement operation is restarted even when the measurement suspension processing was performed by detecting the error in the measurement apparatus 2, and perform the reading of the bar-code information and the matching of the original point position based on the determination result.

In addition, it is also applicable to perform the reading of the bar-code information and the matching of the original point position depending on whether the rotation positions of the reagent table group and the dispensing unit group are changed between the time of completing the initialization operation of the measurement apparatus 2 and the time when the measurement apparatus 2 performs the measurement operation for the first time after the initialization.

Moreover, in the above embodiment, all the bar-code labels of the reagent table group are read in S117 of FIG. 8. However, the present invention is not limited thereto. For example, the present invention may be configured such that a reading of the bar-code labels is performed only for the reagent table, which was moved from the replacement position during the suspension, among the reagent table group, and that the reading range of the bar-code label is changed in accordance with the movement amount from the replacement position.

In the above embodiment, the present invention is applied to the specimen analyzing apparatus for optically measuring and analyzing a specimen (blood) by irradiating a light beam onto a measurement sample prepared by adding the reagent to blood, and using a coagulation method, a chromogenic chromogenic substrate method, an immunoturbidimetric method, and a condensation method. However, the present invention is not limited thereto, and may be applied to a smear preparation apparatus for preparing a sample of a specimen (blood).

In the above embodiment, the determination regarding the movement (S121 to S123 and S202 to S204) and the processing for the returning operation to the original point (S116, S124, and S125) are controlled by the control section 300. However, the present invention is not limited thereto, and it is also applicable that the determination regarding the movement is controlled by the main body 400 and the processing for the returning operation to the original point is controlled by the control section 300.

In addition to the above description, the embodiment of the present invention can be appropriately modified in various manners within the scope of the technical spirit shown in the range of the claims.

What is claimed is:

1. A specimen processing apparatus comprising:
    a specimen processing section which includes a movable section and processes a specimen by moving the movable section automatically; and
    a controller configured to control the specimen processing section to control an automatic moving operation of the movable section, receive a detection result related to a position of the movable section, determine, based on the detection result, whether or not the movable section was moved while the automatic moving operation of the movable section had been stopped, and control the specimen processing section to move the movable section to an original point position by a first moving operation in response to determining that the movable section was not moved while the automatic moving operation of the movable section had been stopped, and control the specimen processing section to move the movable section to the original point position by a second moving operation which is different from the first moving operation in response to determining that the movable section was moved while the automatic moving operation of the movable section had been stopped.

2. The specimen processing apparatus according to claim 1, wherein the movable section comprises a dispensing unit, and the controller is configured to determine whether the dispensing unit was moved based on stop position information regarding a position of the dispensing unit at a time of stopping the automatic moving operation of the movable section and waiting position information regarding a position of the dispensing unit during a stop period of the automatic moving operation of the dispensing unit.

3. The specimen processing apparatus according to claim 1, wherein the movable section comprises a reagent table, and the controller is configured to determine whether the reagent table was moved based on stop position information regarding a position of the reagent table at a time of stopping the automatic moving operation of the movable section and start position information regarding a position of the reagent table at a time of starting the automatic moving operation of the reagent table.

4. The specimen processing apparatus according to claim 1, wherein the controller is configured to control the specimen processing section to suspend a specimen processing operation in response to occurrence of a predetermined suspension event, and determine whether the movable section was moved during a period from the suspension of the specimen processing operation to a restart of the specimen processing operation.

5. The specimen processing apparatus according to claim 4, further comprising an input device,
    wherein the controller is configured to control the specimen processing section to suspend the specimen processing operation in response to a suspension command of the specimen processing operation being input by the input device.

6. The specimen processing apparatus according to claim 4, further comprising an input device,
    wherein the controller is configured to control the specimen processing section to restart the specimen processing operation in response to a restart command of the specimen processing operation being input by the input device.

7. The specimen processing apparatus according to claim 1, wherein:
    the controller is configured to control the specimen processing section to perform an operation for returning the movable section to the original point position; and to control the specimen processing section to start the specimen processing operation by moving the movable section from the original point position automatically.

8. The specimen processing apparatus according to claim 7, wherein the controller is configured to control the specimen processing section to return to the original point position by the first moving operation of a first number of steps to approach the original point position in response to determining that the movable section was not moved while the automatic moving operation of the movable section had been stopped, and control the specimen processing section to return to the original point position by the second moving operation of a second number of steps to approach the original point position in response to determining that the movable section was moved while the automatic moving operation of the movable section had been stopped, the second number being larger than the first number.

9. The specimen processing apparatus according to claim 7, wherein the controller is configured to control the specimen processing section to start a specimen processing operation by moving the movable section automatically in response to determining that the movable section was not moved while the automatic moving operation of the movable section had been stopped.

10. The specimen processing apparatus according to claim 1, wherein:
the movable section includes a reagent dispensing pipette for dispensing a reagent within a reagent container or a specimen dispensing pipette for dispensing the specimen within a specimen container; and
the specimen processing section includes a reagent pipette driving section configured to drive the reagent dispensing pipette or a specimen pipette driving section configured to drive the specimen dispensing pipette.

11. The specimen processing apparatus according to claim 1, wherein:
the movable section includes a container holder for holding a reagent container; and
the specimen processing section includes a container driving section configured to drive the container holder.

12. The specimen processing apparatus according to claim 1, wherein:
the movable section includes a container holder which holds reagent containers;
the specimen processing section includes an identification information obtaining section configured to obtain identification information of the reagent containers held by the container holder; and
the controller is configured to control the identification information obtaining section to obtain the identification information.

13. The specimen processing apparatus according to claim 1, further comprising:
a detector configured to detect an amount of movement of the movable section from the position, from which the movable section was moved while the automatic moving operation of the movable section had been stopped, and the detection result.

14. The specimen processing apparatus according to claim 1, further comprising a detector configured to detect whether the movable section was moved while the automatic moving operation of the movable section had been stopped to replace a reagent container,
wherein the movable section is driven to a stop position in response to the automatic moving operation being stopped, and
the detector is configured to detect a displacement amount of the movable section from the stop position and provide the detection result to the controller.

15. The specimen processing apparatus according to claim 14, further comprising a motor configured to move the movable section and an encoder configured to output positional information indicating an actual position of the motor,
wherein the motor is configured to receive a position command and move the movable section to the stop position corresponding to the position command, and
the detector is configured to detect the displacement amount between the stop position corresponding to the position command and the actual position corresponding to the positional information output by the encoder.

16. A specimen processing apparatus comprising:
a specimen processing section which includes a movable section and processes a specimen by moving the movable section automatically; and
an information processing section, which is configured to monitor the movable section and includes a processor and a memory storing a computer program which, when executed by the processor, causes the processor to be configured to control the specimen processing section to control an automatic moving operation of the movable section, receive a detection result related to a position of the movable section, determine, based on the detection result, whether or not the movable section was moved while the automatic moving operation of the movable section had been stopped, control the specimen processing section to move the movable section to an original point position by a first moving operation in response to determining that the movable section was not moved while the automatic moving operation of the movable section had been stopped, and control the specimen processing section to move the movable section to the original point position by a second moving operation which is different from the first moving operation in response to determining that the movable section was moved while the automatic moving operation of the movable section had been stopped.

17. The specimen processing apparatus according to claim 16, wherein the movable section comprises a dispensing unit, and
the computer program, when executed by the processor, causes the processor to be configured to determine whether the dispensing unit was moved based on stop position information regarding a position of the dispensing unit at a time of stopping the automatic moving operation of the dispensing unit and waiting position information regarding a position of the dispensing unit during a stop period of the automatic moving operation of the dispensing unit.

18. The specimen processing apparatus according to claim 16, wherein the movable section comprises a reagent table, and
the computer program, when executed by the processor, causes the processor to be configured to determine whether the reagent table was moved based on stop position information regarding a position of the reagent table at a time of stopping the automatic moving operation of the reagent table and start position information regarding a position of the reagent table at a time of starting the automatic moving operation of the reagent table.

19. The specimen processing apparatus according to claim 16, wherein the computer program, when executed by the processor, causes the processor to be configured to control the specimen processing section to suspend the specimen processing operation in response to occurrence of a predetermined suspension event, and determine whether the movable section was moved during a period from a suspension of the specimen processing operation to a restart of the specimen processing operation.

20. The specimen processing apparatus according to claim 16, wherein the computer program, when executed by the processor, causes the processor to be configured to control the specimen processing section to perform an operation for returning the movable section to the original point position, and control the specimen processing section to start the specimen processing operation by moving the movable section from the original point position automatically.

21. A specimen processing apparatus comprising:
a specimen processing section which includes a movable section and processes a specimen by moving the movable section automatically; and
a controller configured to determine whether or not the movable section was moved while an automatic moving operation of the movable section had been stopped, and control the specimen processing section to move the movable section to a first position in response to determining that the movable section was moved while the automatic moving operation of the movable section had been stopped, wherein the movable section includes a container holder which holds reagent containers, the specimen processing section includes an identification information obtaining section configured to obtain identification information of the reagent containers, and the controller is configured to control the identification information obtaining section to obtain the identification information of the reagent containers held in a first area of the container holder in response to determining that the movable section was not moved while the automatic moving operation of the movable section had been stopped, and to obtain the identification information of the reagent containers held in a second area in response to determining that the movable section was moved while the automatic moving operation of the movable section had been stopped, the second area including the first area and being larger than the first area.

22. The specimen processing apparatus according to claim 21, further comprising:

a cover which is configured to cover the container holder, and includes a lid section configured to be opened and closed, and the reagent containers which are held in the first area are replaceable through an opening which is formed when the lid section is opened.

* * * * *